United States Patent [19]

King

[11] Patent Number: 5,702,365
[45] Date of Patent: Dec. 30, 1997

[54] DAUL-LUMEN CATHETER

[76] Inventor: Toby St. John King, 28B Cavendish Avenue, Cambridge CB1 4US, United Kingdom

[21] Appl. No.: 674,964

[22] Filed: Jul. 3, 1996

Related U.S. Application Data

[63] Continuation of Ser. No. 387,810, filed as PCT/GB93/01890, Sep. 7, 1993, abandoned.

[30] Foreign Application Priority Data

Sep. 8, 1992 [GB] United Kingdom ............... 9218994

[51] Int. Cl.⁶ ........................................ A61M 25/00
[52] U.S. Cl. ........................................ 604/105; 604/107
[58] Field of Search ........................ 604/104–109, 604/264, 280

[56] References Cited

U.S. PATENT DOCUMENTS

| | | | |
|---|---|---|---|
| 4,154,242 | 5/1979 | Termanini | 604/105 |
| 4,572,186 | 2/1986 | Gould et al. | 128/341 |
| 4,699,611 | 10/1987 | Bowden | 604/51 |
| 5,030,201 | 7/1991 | Palestrant | 604/22 |
| 5,073,166 | 12/1991 | Parks et al. | 609/93 |
| 5,106,363 | 4/1992 | Nobuyoshi | 604/280 X |
| 5,112,310 | 5/1992 | Grobe | 604/175 |
| 5,203,773 | 4/1993 | Green | 604/104 |
| 5,275,610 | 1/1994 | Eberbach | 606/198 |
| 5,421,832 | 6/1995 | Lefebvre | 604/53 |

FOREIGN PATENT DOCUMENTS 955490  4/1964  United Kingdom ............... 604/105

Primary Examiner—Corrine M. McDermott
Attorney, Agent, or Firm—Watson Cole Stevens Davis

[57] ABSTRACT

A dual-lumen blood-treatment catheter has inner and outer lumina open towards the patient end. The catheter has expandable portions in the outer lumen located near the patient end for atraumatically preventing collapse of the blood vessel to ensure free flow of blood into and out of the catheter. In one embodiment, the outer lumen has a plurality of slits around its circumference which form slats therebetween. Withdrawal of the inner lumen relative to the outer lumen causes the slits to open, thereby bowing the slats to expand the outer lumen.

12 Claims, 5 Drawing Sheets

DAUL-LUMEN CATHETER

This is a Continuation of application Ser. No. 08/387,810 filed Feb. 27, 1995, now abandoned.

The present invention relates to a dual-lumen catheter. The dual-lumen catheter of the present invention has particular application for haemodialysis.

Dual-lumen catheters have been proposed for use in haemodialysis and are inserted into a vein, usually the jugular, subclavian or femoral vein. Such dual-lumen catheters have a first, arterial lumen through which blood is withdrawn from the vein. The blood is pumped round a dialysis filtration circuit and returned to the vein through a second, venous lumen of the catheter.

A dual-lumen haemodialysis catheter is usually fixed in situ on the patient for about two weeks, although in some instances the catheter may be in situ for up to eight months. The catheter is normally only removed when treatment is no longer required or in case of infection at the insertion site or due to catheter malfunction.

With such catheters, particularly when used in children, who have relatively narrower and weaker veins than adults, and/or when the catheter is in situ for a relatively long period, collapse of the vein in which the catheter is inserted is a real problem, particularly because it can cause the catheter to be blocked and in any event reduces the efficiency of the catheter and may prevent the catheter from working altogether.

According to the present invention, there is provided a dual-lumen catheter comprising an outer lumen and an inner lumen which are joined at an insertion end of the catheter, the inner lumen lying within the outer lumen, the outer lumen being expandable for atraumatically preventing collapse of a vessel into which the catheter is inserted.

The outer lumen provides a support which prevents collapse of the vessel into which the catheter is inserted. The outer lumen need not necessarily be expanded so far that it contacts the vessel; rather, it will usually be sufficient that the outer lumen be expanded slightly so that it will keep the vessel open should the vessel begin to collapse.

Preferably, the outer lumen has a plurality of slits around its circumference which forms slats therebetween, withdrawal of the inner lumen relative to the outer lumen causing the slits to open thereby bowing the slats to expand the outer lumen.

The use of slits provides a simple mechanism for allowing the outer lumen to be expanded. The slits may also provide an opening through which blood can enter the outer (arterial) lumen.

Means are preferably provided for controllably withdrawing the inner lumen relative to the outer lumen.

The withdrawing means may comprise a linear mechanism, which may be a ratchet mechanism. Alternatively, the withdrawing means may comprise a rotary mechanism. The rotary withdrawing mechanism may comprise a screw thread on the inner lumen and a nut threaded on said inner lumen screw-thread, the nut being rotatable on said screw thread to withdraw and to advance the inner lumen relative to the outer lumen.

As an alternative to providing slits in the outer lumen, the outer lumen may include at least one sac which may be pressurised to expand the outer lumen.

An example of the present invention will now be described with reference to the accompanying drawings, in which.

Figure 1:
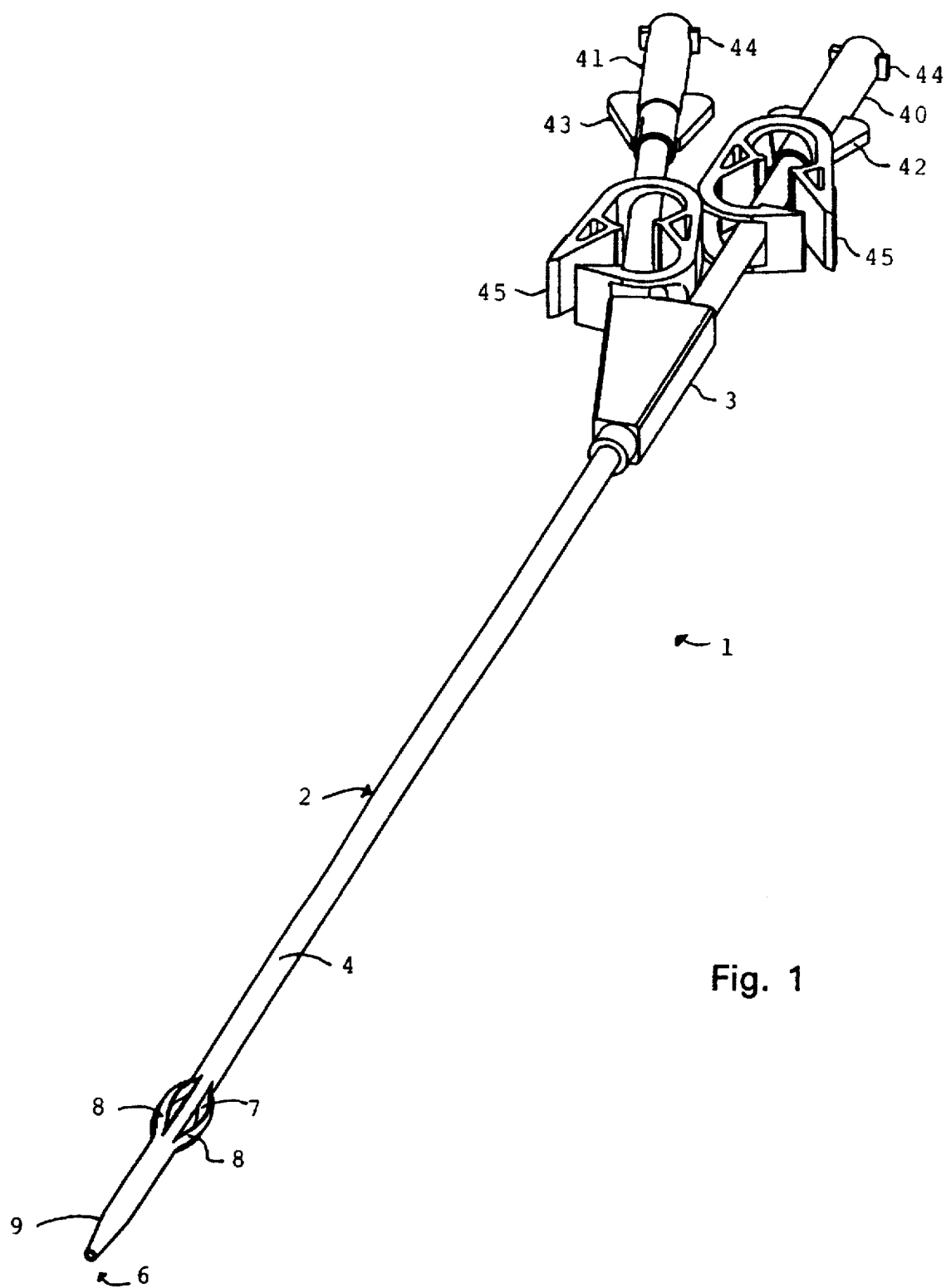
FIG. 1 is a perspective view of a first example of the present invention.

In FIG. 1 to FIG. 4, a catheter 1 includes a blade 2, which consists of the portion of the catheter which is inserted into the body of the patient, and a hub 3.

The blade 2 includes an outer (arterial) lumen 4 and a substantially concentric inner (venous) lumen 5 within the outer lumen 4. The outer and inner lumina 4,5 are joined at the insertion end 6 of the catheter 1. At their other ends, the outer and inner lumina 4,5 enter and are fixed to the hub 3 as will be described in more detail below.

In the first example shown in FIGS. 1 to 4, the outer lumen 4 is provided with a plurality of substantially parallel slits 7. In the example shown, there are six slits 7 around the circumference of the outer lumen 4. The slits 7 in the example shown are parallel to the longitudinal axis of the blade 2, thereby forming six slats 8 which are substantially parallel to the longitudinal axis of the blade 2.

It is to be understood that, in some applications, the slits 7 may spiral around the circumference of the outer lumen 4. Furthermore, more or less than the six slits 7 shown in the example may be used according to particular requirements.

Figure 2:
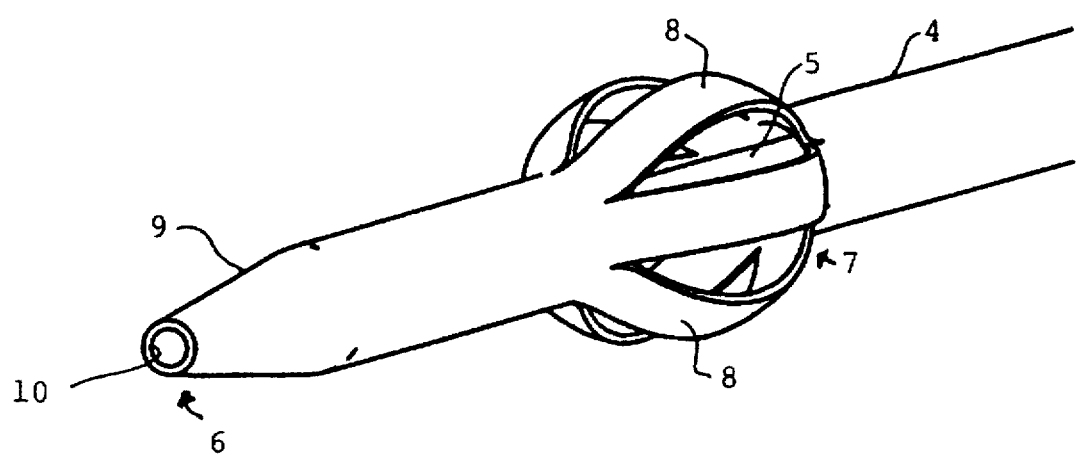
FIG. 2 is a detailed perspective view of the insertion end of the first example.

Because the outer lumen 4 is joined to the inner lumen 5 at the insertion end 6 of the blade 2, withdrawal of the inner lumen 5 with respect to the outer lumen 4 causes the slats 8 to buckle and bow outwards as shown in FIGS. 1 and 2. This bowing of the slats 8 may be facilitated by thinning a portion of one or more of the slats 8 at or towards its centre, for example, which will increase the flexibility of the slat 8 in that region.

In use, the inner lumen 5 is advanced relative to the outer lumen 4 so that the slats 8 are preferably flush with the surface of the remainder of the outer lumen 4. For haemodialysis, the blade 2 of the catheter 1 is then inserted conventionally into the vessel, which is usually one of a jugular, subclavian, or femoral vein. This insertion of the blade 2 is facilitated by the tapered, generally frustoconical shape of the insertion end 6.

Once the blade 2 has been inserted sufficiently far, the inner lumen 5 is withdrawn relative to the outer lumen 4 which causes the slats 8 to bow outwards. It will not normally be necessary for the slats 8 to be bowed outwards so far that they actually exert an outwards force on the vein wall as their primary purpose is not necessarily to expand the vein wall, rather it is to prevent collapse of the vein wall. Accordingly, the overall diameter of the expanded slats 8 will normally be less than the diameter of the vein into which the blade 2 is inserted. Where the diameter of the expanded slats 8 exceeds that of the vein, it is not so large as to cause expansion of the vein beyond its elastic limit, thereby allowing the vein to relax to its natural size when the slats 8 are flattened.

The blade 2 can be formed by extruding the outer and inner lumina 4,5 as tubes. Suitable materials include a thermosoftening polymer such as polyurethane, although other materials such as PTFE may be used. The preferred material is radio-opaque "Teco-Flex" (trade mark) medical grade polyurethane. The outer and inner lumina 4,5 are then joined at the tip 9 of the insertion end 6.

It is preferred that the outer lumen 4 be blocked at the end of the slits 7 proximate the insertion end 6 to prevent blood stagnating in the space otherwise formed between the outer and inner lumina 4,5 at the insertion end 6, thereby preventing infection or clotting of the blood. This can be achieved by putting the tip ends of the outer and inner lumina 4,5 into a mould which is frustoconically shaped to provide the shaped insertion end 6 and injecting material so that it travels up the outer lumen 4 until it reaches the slits 7. The material of the tip 9 of the blade 2 is generally similar to that of the blade 2, but may be a softer grade to produce an atraumatic tip 9 which reduces the risk of tissue damage on insertion of the blade 2.

As an alternative to injecting material up the outer lumen 4, the inner lumen 5 may be provided with a relatively wider section so that, when the inner lumen 5 is inserted into the outer lumen 4, the wider section forms a blockage at the correct location adjacent the ends of the slits 7 proximate the tip 9. A thermoforming process may be used to make this wider section integral with the outer lumen 4.

When the blade 2 is inserted into or withdrawn from a vein, the arrangement is preferably such that the slats 8 are substantially flush with the outer surface of the outer lumen 4 so as to minimise the risk of tissue damage. During dialysis, the slits are opened to allow blood to flow from the vein into the outer lumen 4 through the gaps created by the slits 7 between the slats 8. The degree of opening of the slits 7 can be varied as will be described further below.

The slits 7 may be formed simply by cutting into the outer lumen 4, without removing any material from the outer lumen 4. This would have the advantage that the slits 7 would be completely closed when the inner lumen 5 is fully advanced relative to the outer lumen 4, creating a seal around the expansion area of the outer lumen 4. This may be helpful in preserving the effectiveness of operation of any anti-coagulant injected into the lumina 4,5 between dialysis to prevent thrombosis within the blade 2. Alternatively, the slits 7 may be formed by removing slithers of material which would leave an opening in the outer lumen 4 even in the unexpanded state. This may help in avoiding tissue damage as the slits 7 are being closed prior to removal of the blade 2 from the vein.

Blood removed from the outer lumen 4 is returned, after dialysis, via the inner lumen 5 and returned to the vein through an opening 10 provided in the end of the tip 9. Further openings may be provided in or close to the tip 9 through the side of the blade 2 to facilitate transfer of blood from the catheter 1.

A guidewire may be used when inserting the catheter, the guidewire being inserted into the vein and the catheter then being passed along this guidewire with the wire passing up the centre of the inner lumen 5. The guidewire is then removed from the vein through the inner lumen 5 once the catheter 1 is in position.

Figure 3:
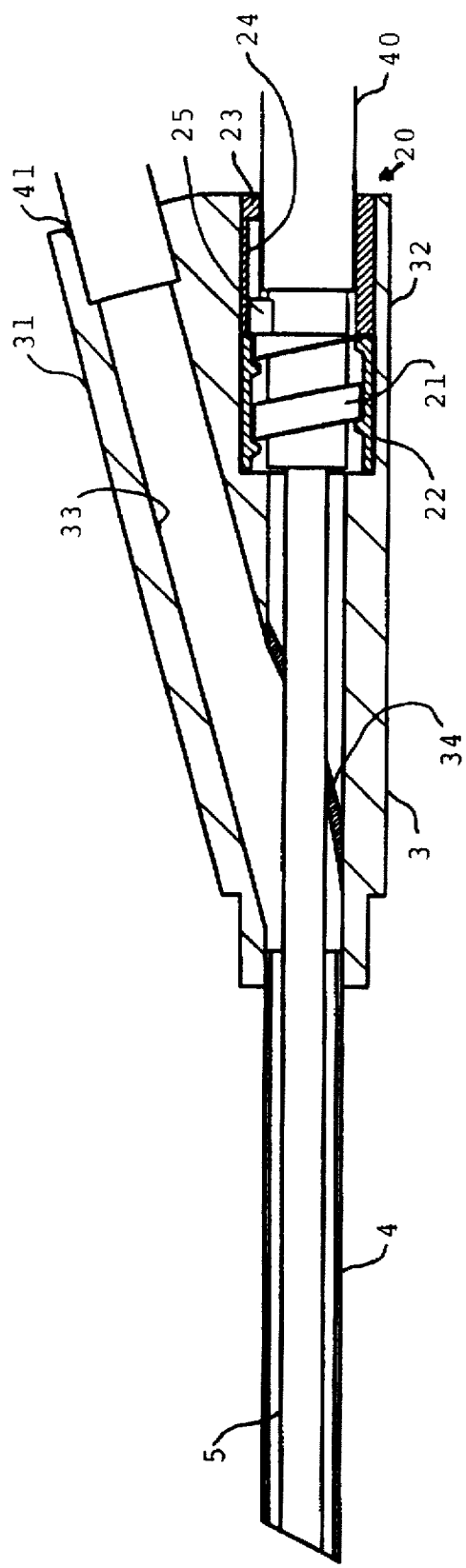
FIG. 3 is a longitudinal cross-sectional view of a first example of a withdrawing mechanism.
Figure 4:
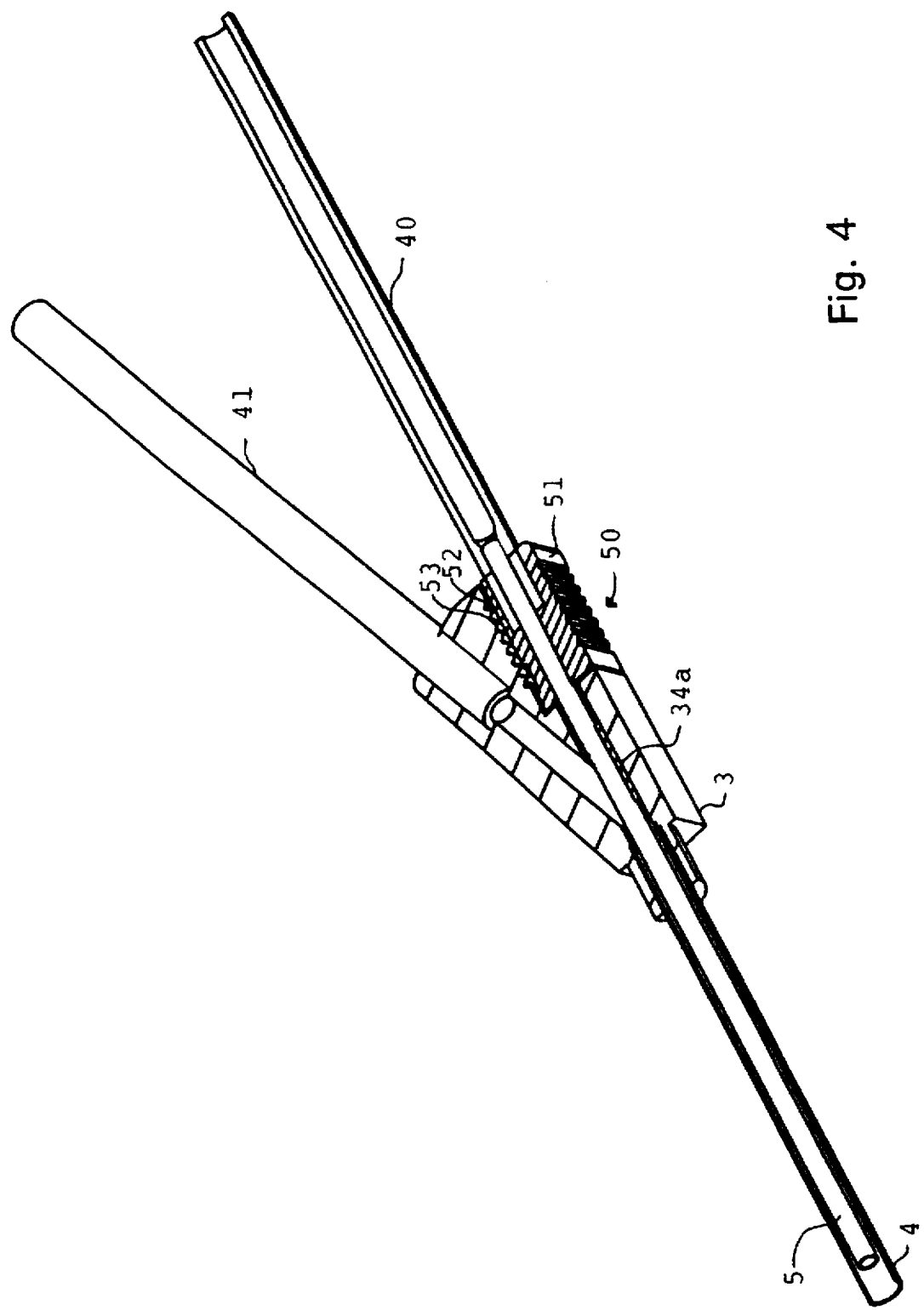
FIG. 4 is a perspective cross-sectional view of a second example of a withdrawing mechanism.

Two examples of mechanisms for moving the inner lumen 5 relative to the outer lumen 4 are shown in FIGS. 3 and 4 respectively.

In FIG. 3, the hub 3 has a generally triangular shape and is hollow along two joined arms 31,32 to form a generally Y-shaped channel. The inner lumen 5 passes through one of the hollow arms 32 to a rotary withdrawing mechanism 20. A screw thread 21 is formed on the end of the inner lumen 5. This screw thread 21 may be cut into or otherwise formed directly on the end of the inner lumen 5 or, alternatively, may be formed on a separate hollow component which is then rigidly fixed to the end of the inner lumen 5. A nut 22 is threaded on the screw thread 21, the nut 22 projecting through the sides of the hub 3.

A plug 23 is fitted in the rear of the hub 3 to retain the rotary withdrawing mechanism 20 within the hub 3. The plug 23 has an elongate guide groove 24 running generally parallel to the direction of travel of the inner lumen 5. A nib 25 is provided on the inner lumen 5 behind the screw thread 21, the nib 25 travelling in the groove 24 which therefore acts as a key-way to prevent rotation of the inner lumen 5 in the hub 3.

As will be understood, the nut 22 can be rotated to withdraw or advance the inner lumen 5 in the hub 3 according to need. It will be seen that the nib 25 has limited travel in the groove 24 defined by the ends of the groove 24, which therefore acts to limit the extent of travel of the inner lumen 5 and accordingly the degree of expansion of the slats 8.

The outer lumen 4 is connected to the channel 33 formed in the other hollow arm 31. This channel 33 is separated from the channel in the first arm 32 by a diaphragm 34 through which the inner lumen 5 passes. This diaphragm 34 separates the concentric lumina 4,5 into two separate blood lines and prevents leakage of blood and aspiration of air as well as being a bacterial seal. The diaphragm 34 may be made of polyurethane produced by a dipping technique to bond the diaphragm between the hub 3 and the inner lumen 5. Alternatively, a natural rubber plug may be provided around the inner lumen 5 in the hollow arm 32 through which the inner lumen 5 passes.

It will be seen that the degree of movement of the inner lumen 5 back and forth relative to the hub 3 can be monitored by determining the number of rotations of the nut 22, for example. Additionally or alternatively, a scale (not shown) may be provided on the back tube 40 which connects the inner lumen 5 to the dialysis machine so that the degree of movement back and forth of the inner lumen 5 can be readily seen.

As an alternative to the rotary mechanism shown in FIG. 3, a linear withdrawing mechanism 50 is shown in FIG. 4. The shape of the hub 3 is generally similar to that of the hub 3 shown in FIG. 3 although in the figure 4 example, an elongate rubber seal 34a is shown.

In this second example, the inner lumen 5 is rigidly fixed to a ratchet block 51 which is provided with a plurality of teeth 52 along one edge. The hub 3 is provided with a corresponding set of teeth 53 over which the teeth 52 on the ratchet block 51 ride. The ratchet block 51 can be retained in the hub 3 by elongate ribs (not shown) on the block 51 running in elongate grooves (not shown) in the hub 3, for example.

To withdraw and advance the inner lumen 5, the ratchet block 51 is simply moved backwards and forwards as required, the teeth 52 on the block 51 riding over the teeth 53 in the hub 3.

In each of the examples shown in FIGS. 3 and 4, friction in the system is likely to be sufficient to prevent collapse of the expanded slats 8, particularly where a rubber seal 34a is used in the hub 3. If necessary, an extra lock can be provided so that the relative positions of the inner and outer lumina 4,5 can be maintained.

As shown in FIG. 1, flanges 42,43 can be provided on the back tubes 40,41 with which the inner and outer lumina 5,4 are respectively in fluid communication, the flanges 42,43 facilitating connection to a blood line. Each of the back tubes 40,41 is terminated with a conventional female luer connector 44. Clamps 45 may also be provided on the back tubes 40,41 and suture wings (not shown) may be provided on or near the hub 3 to allow the catheter to be stitched to a patient's skin.

Figure 5:
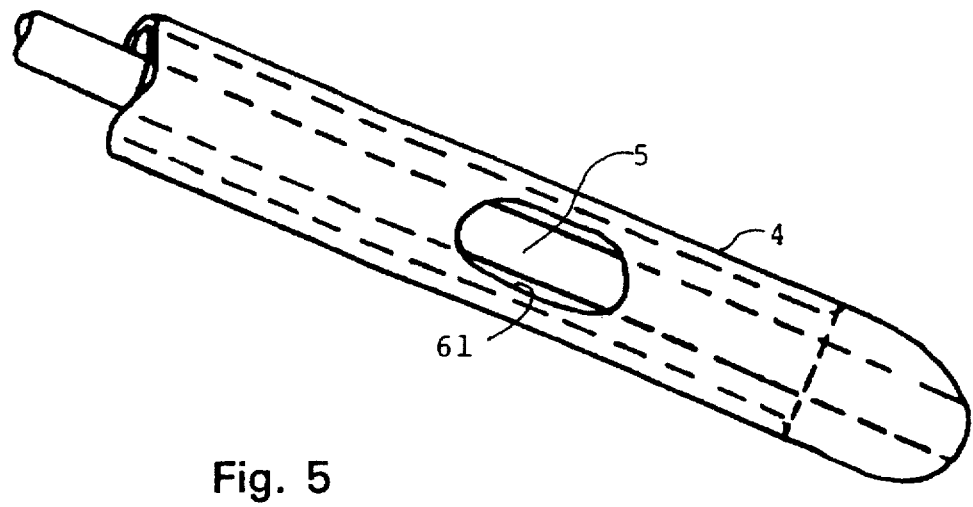
FIG. 5 is a perspective view of a second example of the present invention.
Figure 6:
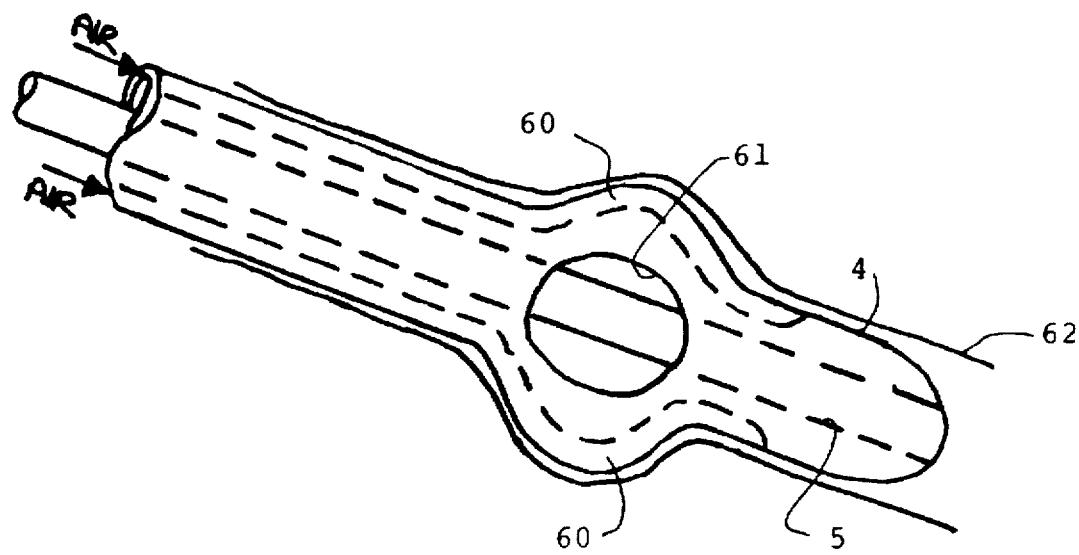
FIG. 6 is a perspective view of the second example in an expanded state.

In the example of the catheter shown in FIGS. 5 and 6, the outer lumen 4 is provided with closed pockets or sacs 60. In the example shown, two diagonally opposite sacs 60 are shown, although more or less sacs may be provided. An opening 61 is provided in the outer lumen 4, the opening 61 allowing withdrawal of blood from the vein 62 in which the catheter 1 is inserted. A similar opening 61 may be provided on the diagonally opposite side of the outer lumen 4. To expand the outer lumen 4, air or another fluid under pressure is introduced into the sacs 60. The material of the outer lumen 4 is elastic, or at least that portion around the hole or holes 61 is elastic, so that the outer lumen 4 expands in this region to prevent the vein 62 from collapsing.

The blade 2 of the catheter 1 of the examples described above, i.e. the portion from the hub 3 to the insertion end 6, may be 120 to 200 mm long, although a paediatric catheter may be shorter. The diameter of the blade 2 would be between about 3.33 to 4 mm; other sizes may be used.

The ends of the slits 7 proximate the insertion end 6 of the catheter 2 may be approximately 30 mm from the insertion end 6 of the catheter 1 and the slits 8 may be 10 to 15 mm long.

I claim:

1. A blood treatment catheter for insertion into a blood vessel of a patient comprising;

an inner tube defining a lumen therewithin, an outer tube disposed in surrounding spaced relationship to said inner tube to define an annular channel between said inner and outer tubes for blood flow therethrough, each of said tubes including a proximal end for connection to blood treatment apparatus and a distal end for insertion into a blood vessel, said distal ends of said inner and outer tubes being directly connected in fixed coaxial relationship to one another to form a tapered tip portion, said inner tube being open at the distal end thereof for permitting blood to flow in a first axial direction from said proximal end of the inner tube through said lumen and out through the open distal end of said inner tube, said outer tube including a flexible expandable portion immediately adjacent to said tip portion at the distal end of the outer tube, means connected to said inner and outer tubes adjacent said proximal end for expanding said expandable portion of the outer tube to prevent collapse of a surrounding blood vessel when the inner tube is moved axially relative to said outer tube towards said proximal end, said expandable portion when in expanded position providing opening means through said outer tube, said opening means including an outer end portion proximate the distal end of said outer tube and an inner end portion spaced from said outer end portion in a direction toward the proximal end of said outer tube, said opening means permitting blood to flow through said opening means into the annular channel between said inner and outer tubes in a direction opposite to said first direction and towards said proximal end of the outer tube, and said tapered tip portion including means for blocking said annular channel adjacent said outer end portion of said opening means for preventing infection or clotting of blood.

2. A catheter according to claim 1, wherein the expanded diameter of the expandable portion is less than the external diameter of the blood vessel in which it is inserted.

3. A catheter according to claim 1 wherein the outer tube has a plurality of slits around its circumference which form slats therebetween, withdrawal of the inner tube relative to the outer tube causing the slits to open thereby bowing the slats to expand the outer tube.

4. A catheter according to claim 3, wherein the slats have a relatively thinner portion to facilitate bowing.

5. A catheter according to claim 3, further comprising means connected between the inner and outer tubes for controllably withdrawing the inner tube relative to the outer tube.

6. A catheter according to claim 5, wherein the withdrawing means comprises a linear mechanism (50).

7. A catheter according to claim 6, wherein the linear withdrawing mechanism (50) is a ratchet mechanism (51, 52,53).

8. A catheter according to claim 5, wherein the withdrawing means comprises a rotary mechanism (20).

9. A catheter according to claim 8, wherein the rotary withdrawing mechanism comprises a screw thread on the inner tube and a nut threaded on said inner tube screw thread, the nut being rotatable on said screw thread to withdraw and to advance the inner tube relative to the outer tube.

10. A catheter according to claim 1 wherein the outer and inner tubes are connected to a hub having a substantially Y-shape channel.

11. A catheter according to claim 10 wherein the inner tube is constrained against rotating in the hub.

12. A wire guided blood treatment catheter for insertion into a blood vessel of a patient along a guide wire comprising:

an inner tube defining a lumen therewithin adapted to slide over the guide wire for facilitating insertion of the catheter with and along a blood vessel, and for carrying blood upon removal of said guide wire, an outer tube disposed in surrounding spaced relationship to said inner tube to define an annular channel between said inner and outer tubes for blood flow therethrough, each of said tubes including a proximal end for connection to blood treatment apparatus and a distal end for insertion into a blood vessel, said distal ends of said inner and outer tubes being directly connected in fixed coaxial relationship to one another to form a tapered tip portion, said inner tube being open at the distal end thereof for permitting blood to flow in a first axial direction from said proximal end of the inner tube through said lumen and out through the open distal end of said inner tube, said outer tube including a flexible expandable portion immediately adjacent to said tip portion at the distal end of the outer tube, means connected to said inner and outer tubes adjacent said proximal end for expanding said expandable portion of the outer tube to prevent collapse of a surrounding blood vessel when the inner tube is moved axially relative to said outer tube towards said proximal end, said expandable portion when in expanded position providing opening means through said outer tube, said opening means including an outer end portion proximate the distal end of said outer tube and an inner end portion spaced from said outer end portion in a direction toward the proximal end of said outer tube, said opening means permitting blood to flow through said opening means into the annular channel between said inner and outer tubes in a direction opposite to said first direction and towards said proximal end of the outer tube, and said tapered tip portion including means for blocking said annular channel adjacent said outer end portion of said opening means for preventing infection or clotting of blood.

* * * * *

UNITED STATES PATENT AND TRADEMARK OFFICE
CERTIFICATE OF CORRECTION

PATENT NO. : 5,702,365
DATED : December 30, 1997
INVENTOR(S) : King

It is certified that error appears in the above-indentified patent and that said Letters Patent is hereby corrected as shown below:

On the title page, item [54] and Column 1, line 1, should read
--       DUAL-LUMEN CATHETER   --

Signed and Sealed this

Third Day of March, 1998

Attest:

BRUCE LEHMAN

*Attesting Officer*      *Commissioner of Patents and Trademarks*